(12) United States Patent
Kitamura (10) Patent No.: US 6,167,578 B1
(45) Date of Patent: Jan. 2, 2001

(54) DEVICE FOR WASHING CROTCH REGION OF PATIENT

(76) Inventor: Teruo Kitamura, No. 75-12, Uematsu-cho, Hamamatsu-shi, Shizouka-ken (JP)

( * ) Notice: Under 35 U.S.C. 154(b), the term of this patent shall be extended for 0 days.

(21) Appl. No.: 09/310,193

(22) Filed: May 12, 1999

(51) Int. Cl.[7] .................................................. A61H 35/00
(52) U.S. Cl. ........................ 4/443; 4/455; 4/456; 607/86
(58) Field of Search ................................ 4/443, 447, 448, 4/450, 453, 455, 456; 601/166; 604/348, 352; 607/86

(56) References Cited

U.S. PATENT DOCUMENTS

| | | | |
|---|---|---|---|
| 473,065 | * | 4/1892 | Duval ........................................ 4/456 |
| 1,362,751 | * | 12/1920 | Snyder ...................................... 4/456 |
| 3,094,983 | * | 6/1963 | MacLeod ................................ 607/86 |
| 3,377,630 | * | 4/1968 | Robare .................................... 607/86 |
| 3,424,160 | * | 1/1969 | Koornwinder et al. ............. 604/352 |
| 3,678,932 | * | 7/1972 | Hudson .................................... 4/444 |
| 4,677,700 | * | 7/1987 | Su ............................................ 5/604 |
| 4,791,686 | * | 12/1988 | Taniguchi et al. ....................... 4/448 |
| 5,447,504 | * | 9/1995 | Baker et al. ........................... 607/86 |
| 5,809,586 | * | 9/1998 | Kitamura ................................. 4/443 |

FOREIGN PATENT DOCUMENTS

| | | | |
|---|---|---|---|
| 107111 | * | 8/1927 | (AT) ....................................... 4/450 |
| 2200033 | * | 7/1973 | (DE) ....................................... 4/443 |
| 9-135876 | * | 7/1973 | (JP) . |

* cited by examiner

Primary Examiner—Charles R. Eloshway
(74) Attorney, Agent, or Firm—Arent Fox Kintner Plotkin & Kahn, PLLC (57) ABSTRACT

A device for washing the crotch region of a patient, including an air chargeable, double-walled soft cover bag capable of forming a washing chamber for accommodating the crotch region of the patient when air is charged into a space between the double walls. A washing liquid injection nozzle is secured within the washing chamber to wash the crotch region. A discharge port is provided in the cover bag to withdraw the washing liquid from the washing chamber. Similar device includes a T-shaped flexible diaper having a looped soft ridge provided on an inside surface thereof. The ridge is contacted with the skin of the patient to define therebetween a washing chamber in which a washing liquid nozzle and air nozzle is provided.

15 Claims, 7 Drawing Sheets

DEVICE FOR WASHING CROTCH REGION OF PATIENT

BACKGROUND OF THE INVENTION

This invention relates to a device for use in evacuation and urination of a patient lying on its back and, more specifically, to a device for washing the pubic and anal regions of the patient after evacuation and/or urination.

U.S. Pat. No. 5,809,586 issued to Kitamura discloses a device for washing the crotch region of a patient which includes a hard base lined with a cushioning material, and a cover lined with a cushioning material and detachably mounted to the base. In the mounted state, a washing chamber is defined between the base and the cover. A washing liquid nozzle is disposed in the washing chamber for washing the crotch region of the patient positioned in the washing chamber.

SUMMARY OF THE INVENTION

It has been found that the above washing device has a problem because it is difficult to raise or turn the body of a patient bearing the washing device.

It is, therefore, an object of the present invention to provide a device for washing the crotch region of a patient which can solve the above problem.

Another object of the present invention is to provide a device of the above mentioned type which permits a patient to put it for a long time without tiring.

In accomplishing the foregoing object, there is provided in accordance with one aspect of the present invention a device for washing the pubic and anal regions of a patient, comprising:

a cover bag including an outer tubular flexible sheet and an inner tubular flexible sheet disposed within said outer sheet to define an air chargeable chamber therebetween, said cover bag having a front side, a rear side and an air charging and discharging port such that said cover bag can assume an inflated state with said inner sheet defining a washing chamber therewithin when air is charged into said air chamber through said port and a deflated state when the air is discharged from said air chamber through said port;

nozzle means secured within said washing chamber for ejecting a washing liquid;

an opening provided in said front side of said cover bag for communicating with said washing chamber;

a pair of holes provided in said rear side of said cover bag for communicating with said washing chamber;

said opening and pair of holes being arranged to receive the lumbar region and the femoral regions of the patient, respectively, when said cover bag assumes said inflated state, such that the pubic region and the anal region of the patient are positioned in said washing chamber and are washed with the washing liquid ejected from said nozzle means;

a front seal member provided on an inside periphery of said opening for sealing said opening receiving the lumbar region of the patient;

a rear seal member provided on an inside periphery of each of said holes receiving the femoral regions of the patient; and discharge port means provided in said cover bag for fluid communication with said washing chamber so that the washing liquid used for washing the pubic and anal regions of the patient is withdrawn from the washing chamber through said discharge port means.

In another aspect, the present invention provides a device for washing the crotch region of a patient, comprising:

a T-shaped flexible diaper member having an outside surface and an inside surface and foldable into a service state in which the crotch region of the patient is surrounded by said diaper member;

a looped soft ridge provided on said inside surface and arranged such that, when the diaper member is in said service state, said ridge is in pressure contact with the skin of the patient to define a washing chamber by the skin of the patient, the inside surface of the diaper member and said ridge with the pubic region and the anal region of the patient being positioned in said washing chamber;

washing liquid injection means secured on said inside surface within said washing chamber for ejecting a washing liquid toward the pubic and anal regions of the patient;

air injection means secured on said inside surface within said washing chamber for injecting air toward the pubic and anal regions of the patient; and a discharge port provided in said diaper member for fluid communication with said washing chamber so that the washing liquid used for washing the pubic and anal regions of the patient is withdrawn from the washing chamber through said discharge port.

BRIEF DESCRIPTION OF THE DRAWINGS

Other objects, features and advantages of the present invention will become apparent from the detailed description of the preferred embodiments of the invention which follows, when considered in the light of the accompanying drawings, in which.

DETAILED DESCRIPTION OF THE PREFERRED EMBODIMENTS OF THE INVENTION

Figure 1:
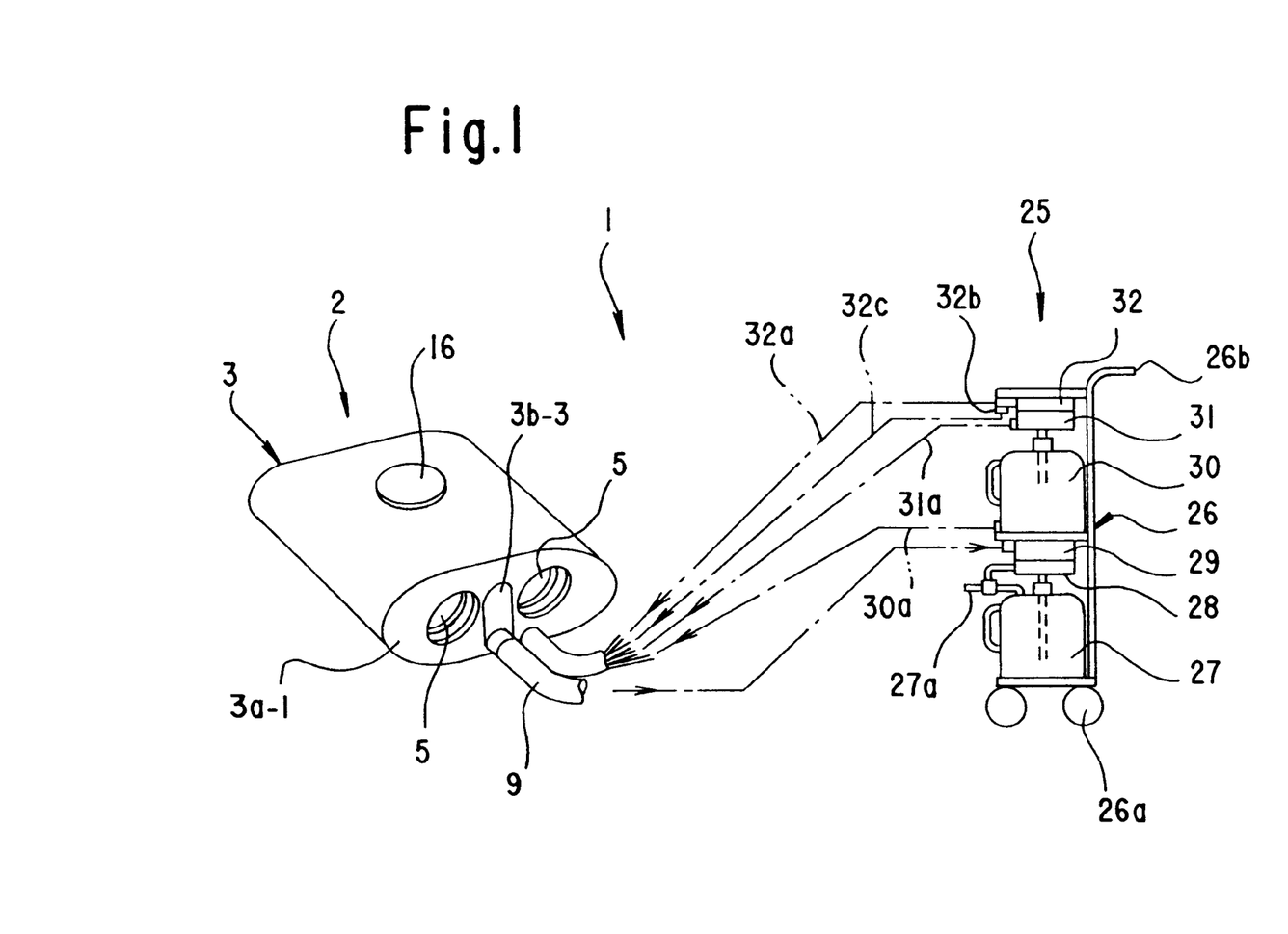
FIG. 1 is a schematic, entire view of the covering device for washing according to the invention.

In FIG. 1, the symbol 1 denotes the device for washing the crotch area of a patient, comprising a wash covering device 2 of a cylindrical shape surrounding the loins 36 and the femurs 37 of a patient 35, and an auxiliary device 25 coupled to the covering device 2.

In FIGS. 1 to 5, the covering device 2 comprises; a washing cover bag 3 which, when filled with pressurized air, forms a specified external shape and a washing chamber 7; a seal member 20 coming into pressing contact with intended parts of the patient 35 for preventing washing liquid from leaking; and nozzles 11 and 12 for spouting washing liquid. The washing cover bag 3 is generally in a cylindrical shape, comprising an outer flexible sheet 3a and an inner flexible sheet 3b forming a closed air chamber 3c to and from which air may be supplied and discharged, and has a loin insertion hole 4 on the front end and a pair of femur insertion holes 5, 5 on the rear end.

Figure 2:
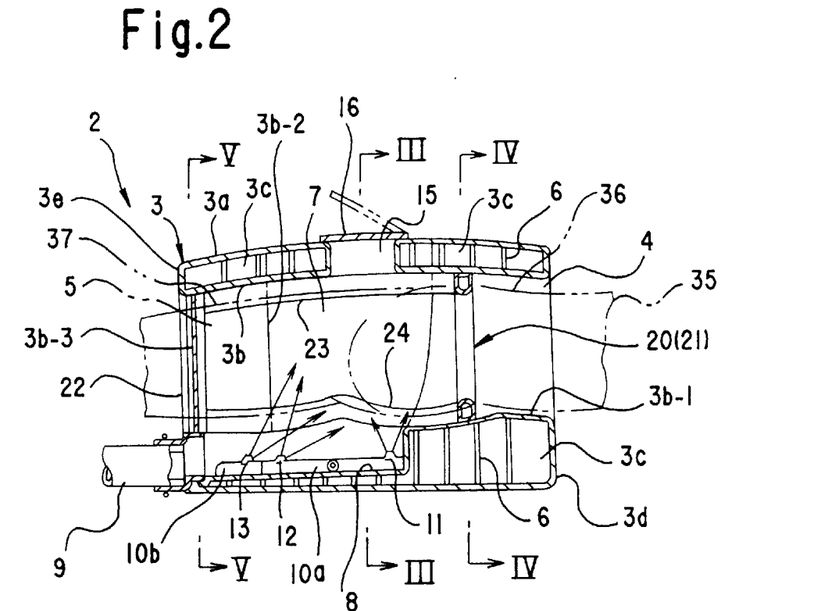
FIG. 2 is a side view of an essential part in cross section of the covering device for washing according to the invention in the state of the device inflated with pressurized air.
Figure 3:
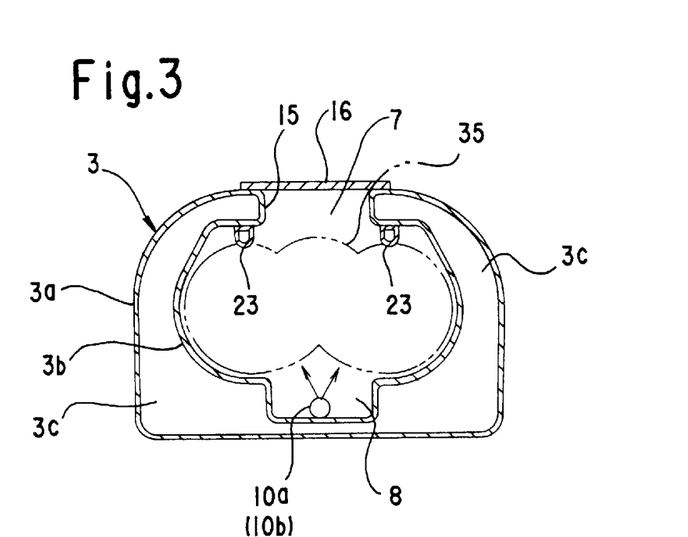
FIG. 3 shows the cross section taken along the line III—III in FIG. 2.

The outer sheet 3a and the inner sheet 3b are made of a material which is highly soft, elastic, and air-tight such as polyethylene containing fibers. The outer sheet 3a is formed in a cylindrical shape straight from the front to the rear end, with the rear end closed with an inward-bent, rear end sheet 3a-1 having a pair of femur insertion holes 5, 5 spaced from each other on the right and left.

The front end 3b-1 of the inner sheet 3b is formed in a cylindrical shape of a small diameter generally along the shape of the abdominal region 36. The rear end 3b-2 of the inner sheet 3b is bifurcated right and left in cylindrical shapes, generally along the shapes of the femurs 37 of the patient 35, and inserted into the femur insertion. holes 5, 5, with their rear ends closed with rear end sheets 3b-3. Thus, a washing chamber 7 of an appropriate capacity is formed in the front-to-rear middle of the inner sheet 3b to surround the anal and pubic regions of the patient 35.

A trough 8 sloping down toward the rear on the back side (underside in FIG. 2) of the rear part of the inner sheet 3b. The rear end of the trough 8 is connected to a water drain pipe (water discharge port) 9. Spout pipes 10a and 10b are disposed to extend in the front-rear directions on the bottom of the trough 8. The front side spout pipe 10a is provided with a first nozzle 11 and a second nozzle 12 for spouting hot water or water. The rear side spout pipe 10b is provided with an air spout 13 for spouting hot air or air. The nozzles are appropriately spaced from each other in the front-rear directions. The first nozzle 11 is directed toward the anal region of the patient 35, the second nozzle toward the pubic region, and the air nozzle 13 toward the area extending from the anal to pubic regions of the patient 35.

The upper part (front side) of the washing chamber 7 is provided with a work hole 15 for admitting a hand of a nursing person. The work hole 15 may be opened or closed with a lid 16. The outer sheet 3a and the inner sheet 3b both forming the air chamber 3c are interconnected through a large number of connection members 6 so that the outer sheet 3a and the inner sheet 3b are inflated in a cylindrical shape when pressurized air is supplied to the air chamber 3c and that the washing chamber 7 is formed as shown in FIGS. 2 to 5.

Figure 4:
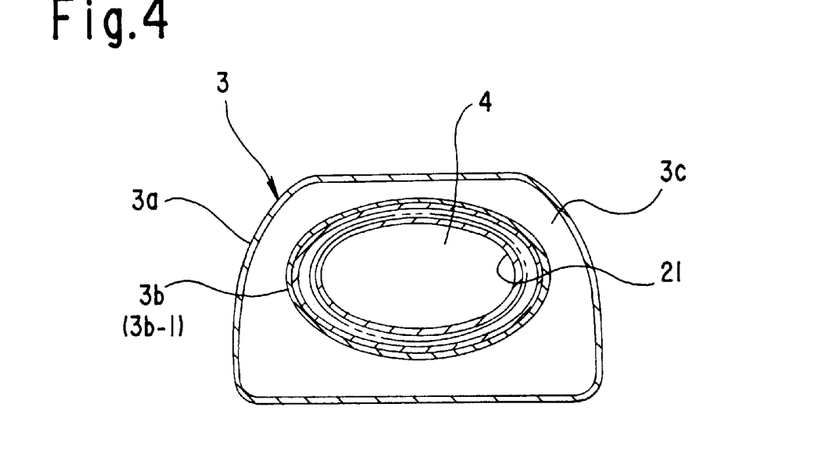
FIG. 4 shows the cross section taken along the line IV—IV in FIG. 2.
Figure 5:
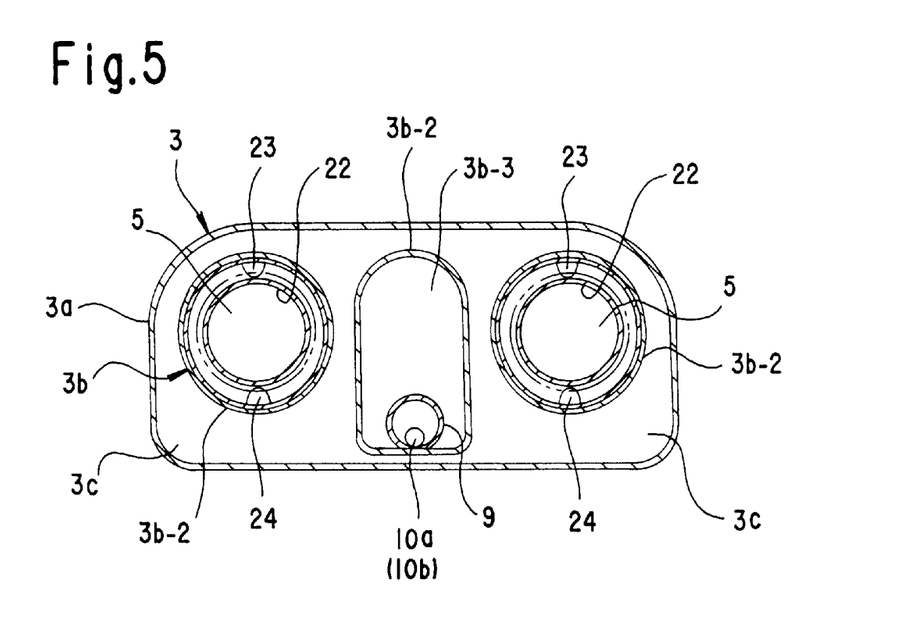
FIG. 5 shows the cross section taken along the line V—V in FIG. 2.
Figure 6:
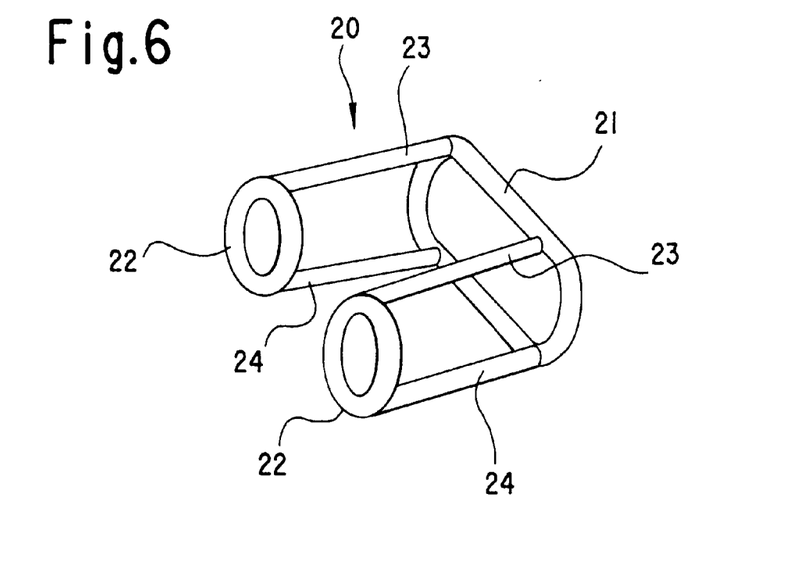
FIG. 6 is a perspective view of a seal member.
Figure 7:
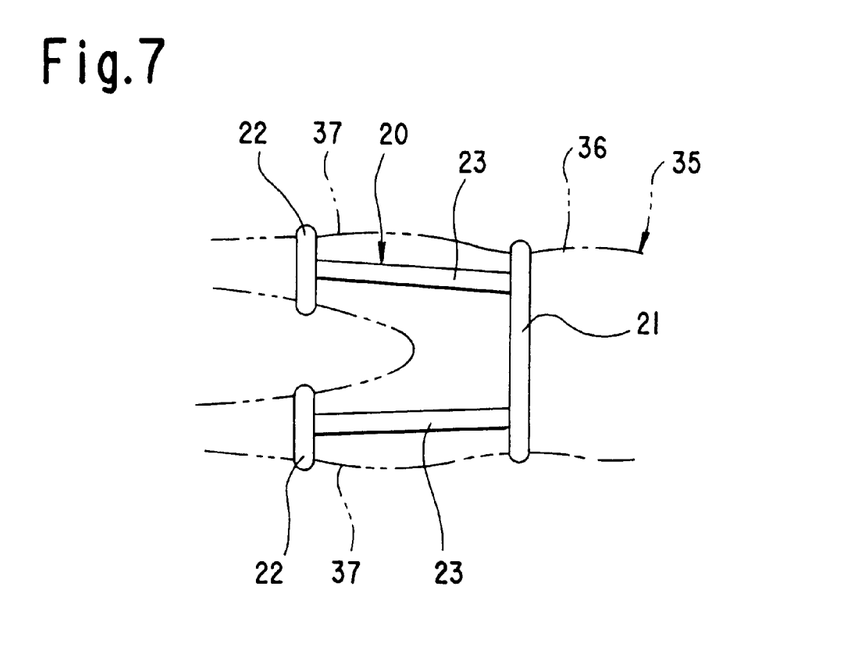
FIG. 7 is a plan view of the seal member.

A seal member (ridge) 20 made of soft air tubes is attached to the inside surface of the washing cover bag 3. As shown in FIGS. 6 and 7, the seal member 20 comprises a front seal 21 of an elliptic shape for fitting around the loins 36 of the patient 35, ring-shaped rear seals 22 for fitting around the femurs 37, upper seals 23 of a straight cylindrical shape interconnecting the internal chambers of the upper (front) right and left corners of the front seal 21 and the upper parts of the rear seals 22, and lower (rear) seals 24 of a straight cylindrical shape interconnecting the internal chambers of the lower right and left corners of the front seal 21 and the lower parts of the rear seals 22. As shown in FIGS. 4 and 5, the front seal 21 and the rear seals 22 are secured to the inside circumferential surfaces of the femur insertion holes 4 and the loin insertion hole 5. The upper seals 23 and the lower seals 24 are secured to the inside circumferential surfaces on the front (upper) side and the rear (lower) side of the area extending from the femur insertion holes 4 to the loin insertion hole 5.

When air of a specified pressure is supplied to the seal member 20, the seal member 20 swells inward and comes into contact with the patient 35 with such an extent of pressure that provides sealing function but does not cause pain to (does not stimulate) the patient 35, seals the periphery of the washing chamber 7, and prevents hot water or water spouted out of the first and second nozzles 11 and 12 from leaking.

As shown in FIG. 1, the auxiliary device 25 comprises a cart 26 carrying on it auxiliary devices such as; a dirty water tank 27, an ozone generator 28, a suction pump 29, a washing (hot) water tank 30, an air pump 31 for washing, and an air pump 32 for the cover, stacked from bottom to top in that order. The dirty water tank 27 is connected through the suction pump 29 to the water discharge pipe 9 of the covering device 2 for washing. The ozone generator 28 is connected to the discharge pipe 27a of the dirty water tank 27. The washing water tank 30 is connected through a water supply pipe 30a to the spout pipe 10a (the first and second nozzles 11 and 12). The air pump 31 for washing is connected through a switching valve (not shown) to the washing water tank 30 and the spout pipe 10b (air spout 13) of the covering device 2. The symbol 31a denotes an air hose connected to the air spout 13.

The covering air pump 32 is connected in parallel through a high pressure hose 32a to the air chamber 3c of the wash covering device 2, and through a low pressure hose 32c to the seal member 20 of the wash covering device 2. FIG. 1 also shows wheels 26a attached to the underside of the cart 26, and the handle 26b of the cart 26. The ozone generator 28, the suction pump 29, the washing air pump 31, and the covering air pump 32 are operated in specified steps as described below by on-off operations of a switch provided near the patient, or by on-off operations of an odor sensor (not shown) provided in the washing chamber 7.

That is, the wash covering device 2 is fitted to the intended part of the patient 35. The air chamber 3c, the first and second nozzles 11, 12, the air spout 13, and the seal member 20 are connected to the specified parts of the auxiliary device 25. Under that condition, when the odor sensor provided in the washing chamber 7 is actuated, the covering air pump 32 works to supply air of a specified high pressure to the air chamber 3c, the washing cover bag 3 inflates in a cylindrical shape and surrounds the loins 36, femurs 37, and buttocks 38 of the patient 35. At the same time, the washing chamber 7 is formed, air of a specified low pressure is supplied to the seal member 20. As a result, the seal member 20 inflates toward the inside, comes into pressing contact with intended parts of the patient 35, and seals the periphery of the washing chamber 7. Here, the pressure of air supplied to the air chamber 3c is of a magnitude that does not cause pain (stimulation) to the patient but still lifts the loins 36, femurs 37, and buttocks 38 of the patient 35. The pressure of air supplied to the seal member 20 is set such that no pain (stimulation) is caused to the patient 35 while providing the sealing function.

Then, the spout of the washing air pump 31 is switched to the washing water tank 30 side to increase the pressure in the washing water tank 30, washing (hot) water in the washing water tank 30 is spouted out of the first and second nozzles 11 and 12 to the anal and pubic regions of the patient 35, and cleans those regions. Along with this, the suction pump 29 and the ozone generator 28 start working to draw dirty water of urination and evacuation from the patient 35 through the water discharge pipe 9 to the dirty water tank 27. The odor coming out of the exhaust pipe 27*a* of the dirty water tank 27 is deodorized by ozone supplied from the ozone generator 28. Here, if necessary, a nursing person assists by hand the washing of the anal and pubic regions of the patient 35 by inserting a hand through the work hole 15 after removing the lid 16 of the washing cover bag 3.

After the above operation for a specified period of time, the spout of the washing air pump 31 is switched to the air spout 13 side to spout air for drying from the air spout 13 to the anal and pubic regions of the patient 35 for a specified period of time to dry those regions. When this operation is over, the covering air pump 32 stops, air in the air chamber 3*c* and the seal member 20 is discharged, the washing cover bag 3 and the seal member 20 shrink and take the shape generally along the bodily shape of the loins 36, femurs 37, and buttocks 38 of the patient 35. Incidentally, since the back side (underside) of the patient 35 is in pressing contact with the back side (lower side) of the washing cover bag 3 due to the patient's own weight, the back side (lower side) of the seal member 20, namely the seals 24 and the back side (lower side) parts of the front seal 21 and the rear seal 22, may be omitted. Also, the seal member 20 may be formed with any highly elastic material such as sponge, gel, or soft urethane in place of the air tube. In that case, it is unnecessary to connect the covering air pump 32 to the seal member.

As is clear from the above explanation, the washing cover bag of this invention makes it possible to dispose of evacuation and urination of a patient lying on bed and to carry out washing of the crotch area including the anal and pubic regions of the patient remaining in bed. Since the washing cover bag takes the shape of a sheet when the evacuation and urination is over and generally follows the body shape of the patient, the patient may be overturned or made to sit upright on bed with the cover remaining attached.

Another embodiment of the invention will be hereinafter described in reference to the appended drawings. In FIGS. 8 through 13, the symbol 101 denotes a cover made of a water-impermeable, flexible sheet material such as a polyethylene sheet for disposing of a patient's evacuation. The cover 101 integrally comprises a main cover 101*a* surrounding part of the patient (P) extending from the back of the loins through the crotch to the lower belly, and side covers 101*b* extending from the front part of the main cover 101*a* in both side directions and surrounding the sides of the loins and the lower belly of the patient (P), and formed in a generally T-shape (like a diaper).

Figure 13:
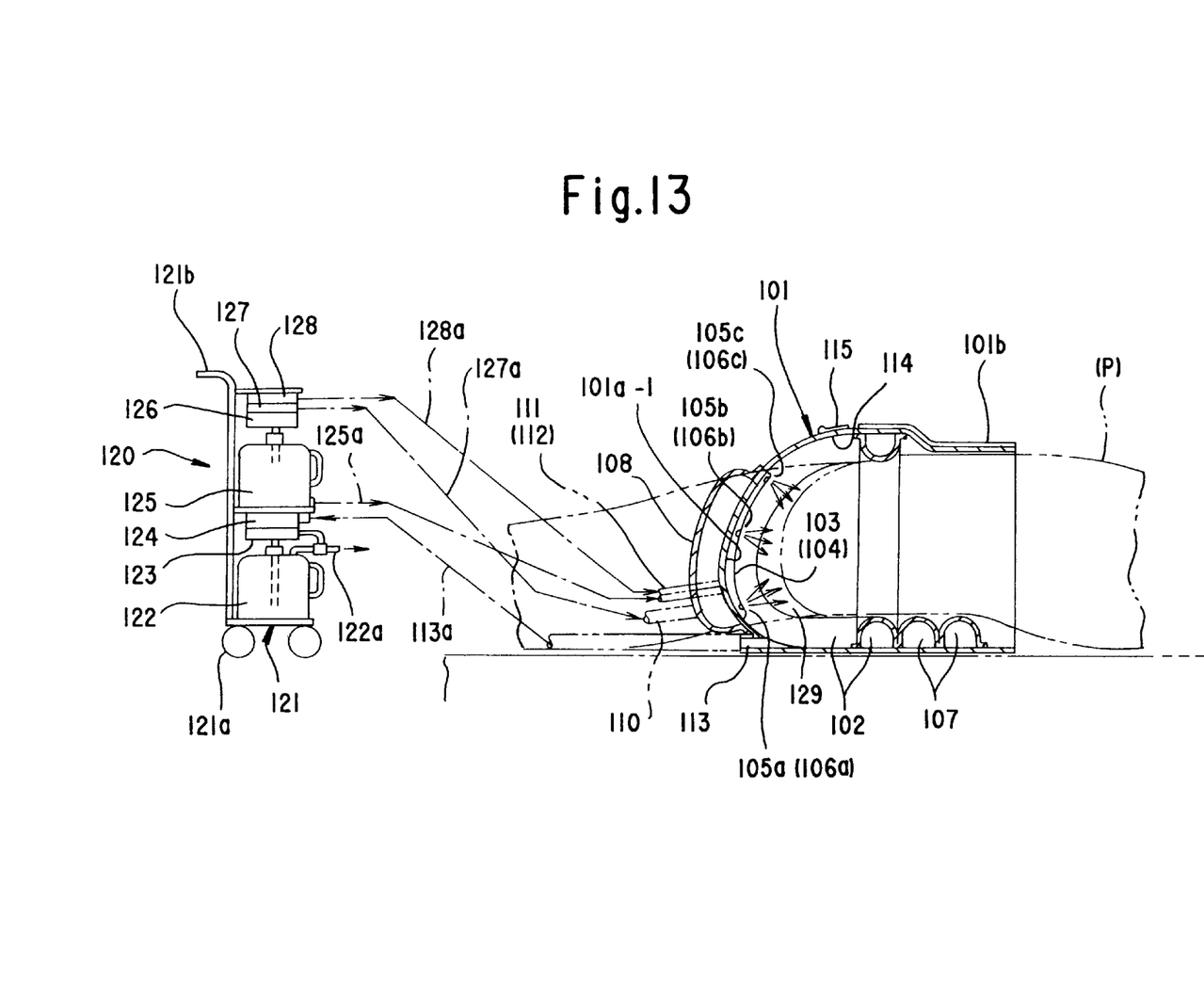
FIG. 13 is a cross-sectional view of the cover in use as seen from the line XIII—XIII in FIG. 12.

A seal member 102 of a frame (annular) shape oblong in the front-and-rear directions is disposed on part of the inside (front) surface of the main cover 101*a* corresponding to the area surrounding the evacuation area of the patient (P). The seal member 2 comprises an air bag (a first air bag) and, when inflated by supplying air into it, comes into contact with the skin of the area around the evacuation area of the patient (P) and causes the inside circumferential part 101*a*-1 of the main cover 101 facing the evacuation area of the patient (P) to move outward away from the evacuation area of the patient (P) as shown in FIG. 13. A water flow passage 103 and an air flow passage 104 are formed parallel to each other to extend in front-and-rear directions in the center of the inside circumferential part 101*a*-1. The front and rear end parts and the front-rear directional central part of those passages are provided with washing liquid spouts 105 (105*a*, 105*b* and 105*c*) and air spouts 106 (106*a*, 106*b* and 106*c*) through which washing water and air (hot air) are spouted to the evacuation area of the patient (P).

Figure 8:
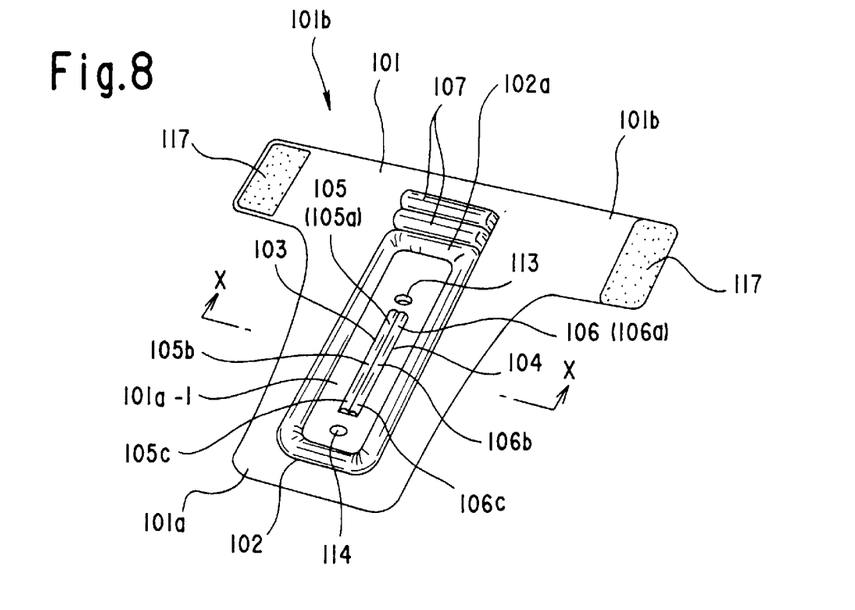
FIG. 8 is a front oblique view of an unfolded cover with its air bag portion inflated.
Figure 9:
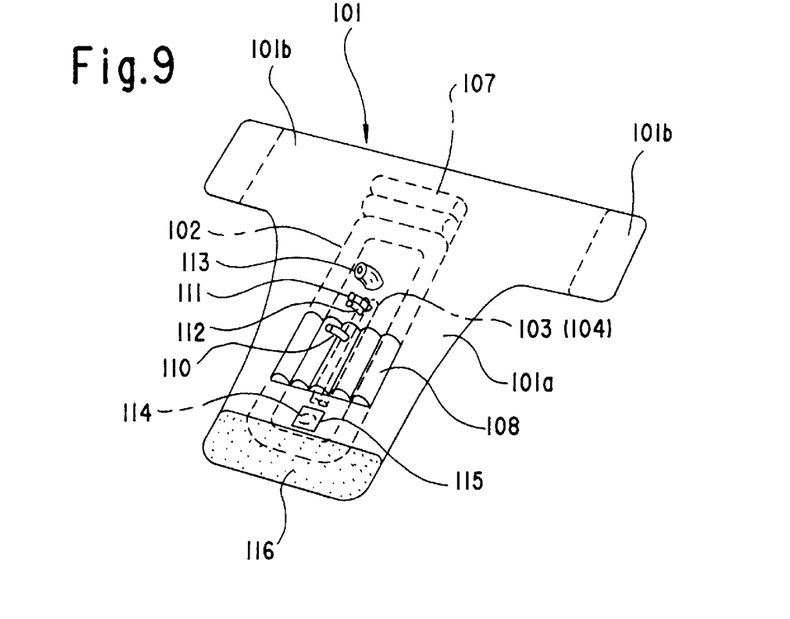
FIG. 9 is a back oblique view of the cover shown in FIG. 8.

Part of the inside (front) surface of the cover 101 corresponding to the buttocks of the patient (P) is formed with a support member (a second air bag) 107, and part of the outside (back) surface of the cover 101 corresponding to the crotch of the patient (P) is formed with a crotch widening member (a third air bag) 108 as shown in FIG. 9. The support member 107 as shown in FIG. 8 comprises a plural number, for example two, of slender air bags (air cylinders) extending in the right-left directions over the front end 102*a* of the seal member 102 and parallel to the front end 102*a*. The crotch widening member (the third air bag) 108 is constituted as shown in FIG. 9: a plural number, for example five, of slender air bags (air cylinders) extending in the vertical direction are arranged side by side parallel to each other in the lower area of the main cover 101*a*. The crotch widening member 108 may also be constituted that the plural number of slender air bags extending in the right-left directions are arranged with one over another parallel to each other in the lower area of the main cover 101*a*.

Figure 10:
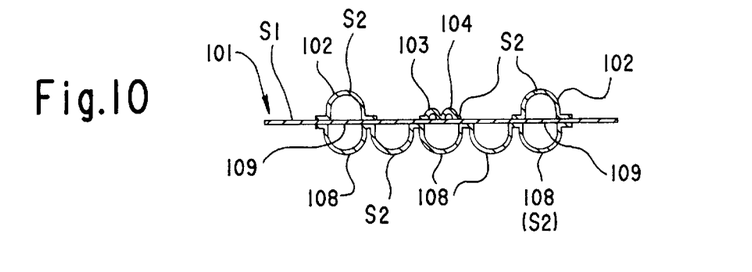
FIG. 10 is a cross-sectional view as seen from the line X—X in FIG. 8.
Figure 11:
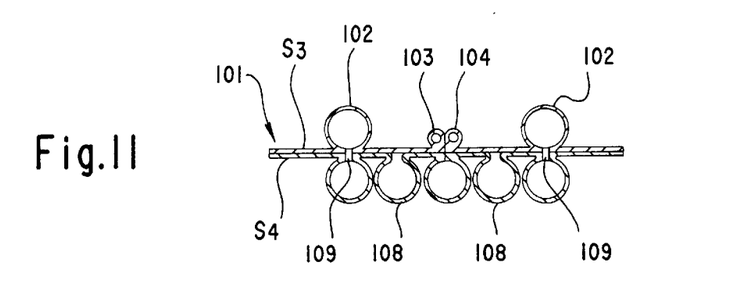
FIG. 11, corresponding to FIG. 10, is a cross-sectional view of a cover of another embodiment.

The seal member 102, the support member 107, the crotch widening member 108, the water flow passage 103, and the air flow passage 104 are formed as shown in FIG. 10. A base sheet $S_1$ of a thermoplastic sheet material is formed in the shape of a diaper. An auxiliary sheet $S_2$ of a similar material is cut to a specified size, bent in a U-shape in one direction (or in the other direction), and its peripheries are heat-welded together. Alternatively, they may be formed as shown in FIG. 11. An inside sheet $S_3$ and an outside sheet $S_4$ of a thermoplastic material are formed in the shape of a diaper, specified parts of them are bent in the U-shape in one direction (or in the other direction), and its peripheries are heat-welded together.

The internal spaces of the seal member 102, support member 107, and the crotch widening member 108 are interconnected through communication holes 109 (shown in FIGS. 10 and 11). As shown in FIG. 9, a first connection port 110 is formed on the outer side of the crotch widening member 108. Third connection ports 111 and 112 are formed on the outer side of the water flow passage 103 and the air flow passage 104. A water drain connection port (water drain port) 113 is formed on the front side of the inside circumferential part 101*a*-1. An air discharge port 114 is formed on the back side of the inside circumferential area 101*a*-1. The first connection port 110, the second and third connection ports 111 and 112, the water drain port 113, and the air discharge port 114 are formed in positions, corresponding to the crotch region, that are less likely to come into contact with the patient (P). In FIG. 9 are shown; a valve 115 made of a sheet material for opening and closing the air discharge port 114 by accessing from outside, and a surface fastener 116 attached to the outside surface of the rear end of the main cover 101*a*. In FIG. 8 are shown surface fasteners 117, 117 attached to the inside surfaces of the outside ends of the side covers 101*b*. Incidentally, the inside surface of the inside circumferential part 101*a*-1 is coated with a water repellent material such as Teflon (by trade name) to prevent water from adhering. Other inside surfaces of the cover 101 (surfaces coming into contact with the patient) are treated by piling or the like for comfortable skin-contact feeling.

Figure 12:
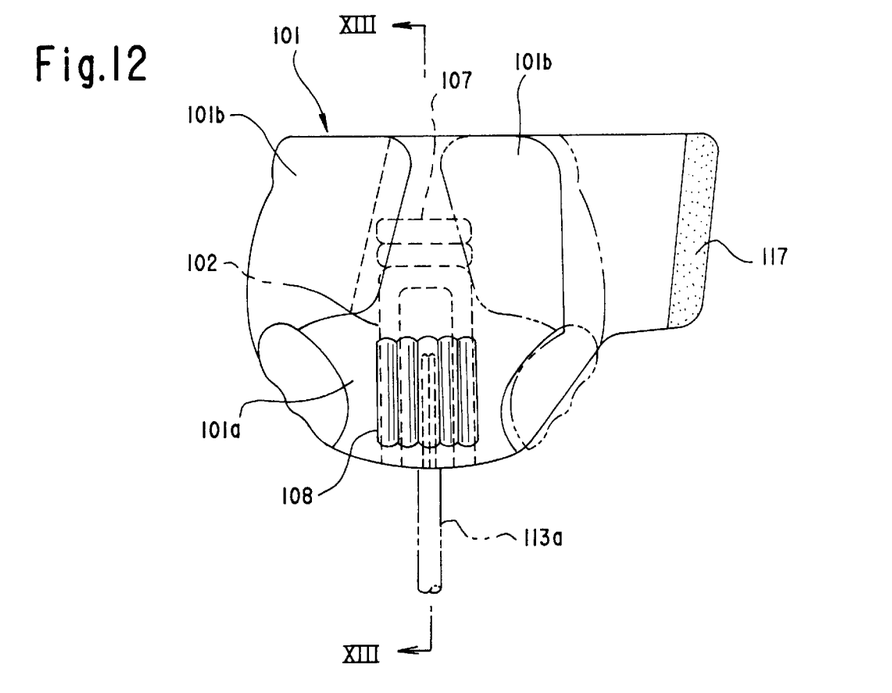
FIG. 12 shows the manner of folding the cover.

The cover 101 formed as described above for disposing of the evacuation is used as shown in FIGS. 12 and 13. The rear half part of the main cover 101a is folded toward the front so as to enclose the evacuation area of the patient (P). Next, the right and left side covers 101b, 101b are folded toward the directions approaching each other, and their surface fasteners 117, 117 are matched with the surface fastener 116 on the main cover 101. Then, the cover 101 is coupled to the auxiliary unit 120 to dispose of the evacuation of the patient (P).

The auxiliary unit 120 is constituted as shown in FIG. 13: a cart 121 carries on it auxiliary devices such as; a dirty water tank 122, an ozone generator 123, a suction pump (suction device) 124, a washing (hot) water tank 125, an air pump (a first air supplying device) 127 for the air bag, and an air pump (a second air supplying device) 128 for drying, stacked from bottom to top in that order. The dirty water tank 122 is connected through the suction pump 124 and a water discharge hose 113a to the water discharge connection port 113 of the cover 101. The ozone generator 123 is connected to the discharge pipe 122a of the dirty water tank 122. The washing water tank 125 is connected through a water supply hose 125a and the second connection port 111 to the water flow passage 103 (washing water spout 105) of the cover 101. The air pump 126 for supplying washing water supplies air of a specified pressure to the washing water tank 125. By means of the pressurized air, washing water in the washing water tank 125 is supplied through the water supply pipe 125a and the second connection port 111 to the water flow passage 103.

The air pump 127 for the air bag supplies air of a specified pressure to the crotch widening member (the third air bag) 108 through an air hose 127a, and the first connection port 110. The pressurized air supplied to the crotch widening member 108 flows through the communication holes 109 (shown in FIGS. 10 and 11) into the seal member 102, and into the support member (the second air bag) 107. The air pump 128 for drying supplies air (or hot air) to the air flow passage 104 through an air hose 128a and the third connection port 106, and spouts the air through the air spouts 106. FIG. 13 also shows wheels 121a attached to the underside of the cart 121, and a handle 121b of the cart 121.

The auxiliary unit 120 is operated in specified steps as describe below when a controller is operated with a switch located at hand of the patient (P) or with an odor sensor (not shown) provided in the cover 101. That is, when the switch at hand of the patient (P) is operated or the odor sensor disposed in the cover 101 is actuated, first the air pump 127 for the air bag is operated to supply air of a specified high pressure to the crotch widening member (third air bag) 108, the seal member. (first air bag) 102, and the support member (second air bag) 107. As a result as shown in FIG. 13, the seal member 102, support member 107, and the crotch widening member 108 are inflated in a cylindrical shape. The inside circumferential area 101a-1 of the cover 101 is moved outward with the frame-like seal member 102, so that a specified space, namely a washing space is formed with part of the inside circumferential area facing the evacuation area of the patient (P). As the seal member 102 comes into contact with intended parts of the patient (P), the washing space is isolated from outside. The buttocks of the patient (P) is raised with the support member 107, and the crotch of the patient (P) is widened with the crotch widening member 108, so that the evacuation and urination of the patient (P) are made easier.

When a preset time elapses in that state, the air pump 126 for supplying washing water is operated, the pressure in the washing water tank 125 is increased, and the washing water (or hot water) in the washing water tank 125 is supplied in an amount such as 500 cc through the water supply hose 125a to the water flow passage 103, and spouted through the water spouts 105a, 105b and 105c to the evacuation area of the patient (P) to wash that area. Along with this, the suction pump 124 and the ozone generator 102 are operated to draw dirty water produced by the evacuation and urination of the patient (P) through a water drain hose 113a into the dirty water tank 122. At the same time, odor in the air discharged from the air discharge pipe 121a of the dirty water tank 122 is deodorized by ozone produced with the ozone generator 123.

When a preset time elapses in that state, the air pump 126 for supplying washing water is stopped, and further after about 130 seconds, the suction pump 124 is stopped. Now the air pump 128 for drying is operated so that air (or hot air) is supplied through an air hose 128a to the air flow passage 104, and the air is spouted out of the air spouts 106a, 106b, and 106c for a certain period of time, for example 10 to 15 seconds, to the evacuation area of the patient (P) to dry that area. Here, the valve 115 is opened by the internal pressure so that the damp air in the washing space is discharged outside through the air discharge port 114.

When a preset time elapses in that state, the air pump 128 for drying is stopped, and then the air pump 127 for the air bag is stopped. The air in the seal member 102, the support member 107, and the crotch widening member 108 is allowed to flow out naturally, so that those members shrink into the shape of a sheet. Incidentally, in the case of a patient (P) who is highly conscious such as a patient (P) of a bone fracture, it may be arranged that the air pump 127 for the air bag, the suction pump 124, the air pump 126 for supplying washing water, and the air pump 128 for drying are operated in specified steps at the patient's discretion.

Here, it may also be arranged that the seal member 102, the support member 107, and the crotch widening member 108 are made of a soft elastic material such as sponge, elastic rubber, or viscous material such as a gel-like material or clay. In that way, the air pump 127 for the air bag may be omitted to simplify the auxiliary unit 120, although the mobility of the inside circumferential area 101a-1 of the cover 101 is slightly reduced.

As is clear from the above description, this invention makes it possible to carry out safe and easy disposal of evacuation and urination of a patient remaining in bed on his or her back, and cleaning of the evacuation area of the patient's body including crotch. Furthermore, since the seal member provided on the cover is made of a soft material, it is easy to turn the patient lying in bed upside down or make the patient sit upright in bed after the evacuation and urination. Since the cover is made in the shape of a diaper, the cover is inexpensive and easy to be put on or removed from the patient.

What is claimed is:

1. A device for washing the pubic and anal regions of a patient, comprising:

a cover bag including an outer tubular flexible sheet and an inner tubular flexible sheet disposed within said outer sheet to define an air chargeable chamber therebetween, said cover bag having a front side, a rear side and an air charging and discharging port such that said cover bag can assume an inflated state with said inner sheet defining a washing chamber therewithin when air is charged into said air chamber through said port and a deflated state when the air is discharged from said air chamber through said port;

nozzle means secured within said washing chamber for ejecting a washing liquid;

an opening provided in said front side of said cover bag for communicating with said washing chamber;

a pair of holes provided in said rear side of said cover bag for communicating with said washing chamber;

said opening and pair of holes being arranged to receive the lumbar region and the femoral regions of the patient, respectively, when said cover bag assumes said inflated state, such that the pubic region and the anal region of the patient are positioned in said washing chamber and are washed with the washing liquid ejected from said nozzle means;

a front seal member provided on an inside periphery of said opening for sealing said opening receiving the lumbar region of the patient;

a rear seal member provided on an inside periphery of each of said holes receiving the femoral regions of the patient; and discharge port means provided in said cover bag for fluid communication with said washing chamber so that the washing liquid used for washing the pubic and anal regions of the patient is withdrawn from the washing chamber through said discharge port means.

2. A device as claimed in claim 1, further comprising an air injection nozzle secured within said washing chamber for injecting air toward the pubic and anal regions of the patient.

3. A device as claimed in claim 1, wherein said cover bag includes a top opening to permit a person's hand to insert into said washing chamber therethrough, and a lid for opening and closing said top opening.

4. A device as claimed in claim 1, wherein each of said front and rear seal members is an annular air tube inflatable upon being charged with air.

5. A device as claimed in claim 4, further comprising a plurality of air tubes each extending between said front and rear seal members for fluid communication with each other.

6. A device for washing the crotch region of a patient, comprising:

a T-shaped flexible diaper member having an outside surface and an inside surface and foldable into a service state in which the crotch region of the patient is surrounded by said diaper member;

an inflatable looped soft ridge provided on said inside surface and arranged such that, when the diaper member is in said service state, said ridge is in pressure contact with the skin of the patient to define a sealed washing chamber by the skin of the patient, the inside surface of the diaper member and said ridge with the pubic region and the anal region of the patient being positioned in and surrounded by said washing chamber;

washing liquid injection means secured on said inside surface within said washing chamber for ejecting a washing liquid toward the pubic and anal regions of the patient;

air injection means secured on said inside surface within said washing chamber for injecting air toward the pubic and anal regions of the patient; and a discharge port provided in said diaper member for fluid communication with said washing chamber so that the washing liquid used for washing the pubic and anal regions of the patient is withdrawn from the washing chamber through said discharge port.

7. A device as claimed in claim 6, wherein said ridge is an air tube.

8. A device as claimed in claim 6, wherein said ridge is made of an elastic material.

9. A device as claimed in claim 6, wherein said ridge is made of a soft deformable solid.

10. A device as claimed in claim 6, wherein said ridge is in the form of a continuous loop.

11. A device as claimed in claim 6, wherein said diaper member comprises a first flexible sheet, a second flexible sheet partly bonded to said first sheet to define an air chargeable chamber between said first and second sheets at a portion at which said first and second sheets are not bonded to each other, and an air inlet port formed in said first sheet for fluid communication with said air chargeable chamber, so that said air chargeable chamber is inflated upon being charged with air through said port to form said ridge.

12. A device as claimed in claim 11, further comprising air feeding means connected to said air inlet port for feeding air to said air chargeable chamber, washing liquid feeding means connected to said washing liquid injection means, suction means connected to said discharge port, and air introducing means connected to said air injection means for supplying air thereto.

13. A device as claimed in claim 6, wherein said diaper member comprises:

a first flexible sheet, a second flexible sheet partly bonded to said first sheet to define first and second air chargeable chambers and a water chargeable chamber between said first and second sheets at portions at which said first and second sheets are not bonded to each other, a first air inlet port formed in said diaper member for fluid communication with said first air chargeable chamber so that said first air chargeable chamber is inflated upon being charged with air through said first air inlet port to form said ridge, at least one air outlet port and a second air inlet port formed in said diaper member for fluid communication with said second air chargeable chamber so that said second air chargeable chamber forms said air injection means and is inflated upon being charged with air through said second inlet port to inject the air from said air outlet port, a water inlet port and at least one water outlet port formed in said diaper member for fluid communication with said water chargeable chamber so that said water chargeable chamber forms said washing liquid injection means and is inflated upon being charged with the washing liquid through said inlet port to inject the washing liquid from said outlet port.

14. A device as claimed in claim 6, further comprising a soft support member formed on said inside surface for supporting engagement with the gluteal regions of the patient.

15. A device as claimed in claim 6, further comprising soft support means formed on said outside surface for facilitating spread of the femoral regions of the patient.

* * * * *